United States Patent
Baumgart

(10) Patent No.: US 8,737,713 B2
(45) Date of Patent: May 27, 2014

(54) SYSTEM FOR FRAME SELECTION FOR OPTIMAL REGISTRATION OF A MULTI-FRAME DATASET

(75) Inventor: John Baumgart, Hoffman Estates, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 247 days.

(21) Appl. No.: 13/196,936

(22) Filed: Aug. 3, 2011

(65) Prior Publication Data

US 2012/0134567 A1  May 31, 2012

Related U.S. Application Data

(60) Provisional application No. 61/417,944, filed on Nov. 30, 2010.

(51) Int. Cl.
*G06K 9/00* (2006.01)
*A61B 5/04* (2006.01)

(52) U.S. Cl.
USPC .......................................... 382/132; 600/509

(58) Field of Classification Search
USPC ................... 382/132; 600/509, 513
See application file for complete search history.

(56) References Cited

U.S. PATENT DOCUMENTS

| | | | |
|---|---|---|---|
| 5,954,650 A | 9/1999 | Saito et al. | |
| 6,438,196 B1 * | 8/2002 | Cesmeli | 378/8 |
| 6,941,323 B1 | 9/2005 | Galperin | |
| 7,660,383 B2 | 2/2010 | Sakaguchi | |
| 7,742,629 B2 | 6/2010 | Zarkh et al. | |
| 2006/0257012 A1 * | 11/2006 | Kaufman et al. | 382/131 |
| 2007/0255150 A1 * | 11/2007 | Brodnick | 600/509 |
| 2007/0265522 A1 * | 11/2007 | Kassai et al. | 600/411 |
| 2008/0009733 A1 * | 1/2008 | Saksena | 600/443 |
| 2008/0107233 A1 * | 5/2008 | Sakaguchi et al. | 378/91 |
| 2008/0281218 A1 * | 11/2008 | Lei et al. | 600/523 |
| 2009/0097731 A1 * | 4/2009 | Sanada et al. | 382/132 |
| 2009/0234239 A1 * | 9/2009 | Shani et al. | 600/516 |
| 2011/0135176 A1 * | 6/2011 | Lendl | 382/130 |

OTHER PUBLICATIONS

Schafer et al., "Three-dimensional reconstruction of coronary stents in vivo based on motion compensated x-ray angiography", Medical Imaging 2007: Visualization and Image-Guided Procedures, Proc. of SPIE vol. 6509, 65091M, 2007.*

* cited by examiner

*Primary Examiner* — Vu Le
*Assistant Examiner* — Soo Park
(74) *Attorney, Agent, or Firm* — Brennan K Bradley

(57) ABSTRACT

An Angiographic X-ray imaging system provides enhanced image feature visualization. At least one repository includes data representing a sequence of X-ray images of a portion of patient anatomy acquired over a time interval and signal data representing electrical activity of the heart of the patient over the time interval. An image data processor determines for individual images of the sequence of X-ray images, characteristics of a portion of the signal data associated with a corresponding image. The characteristics comprise at least one of, (a) a peak to peak value of a portion of the signal data associated with a corresponding image and (b) an average value of a portion of the signal data associated with the corresponding image. The image data processor selects a set of images exclusive of particular images from the sequence of X-ray images in response to the determined characteristics and generates an averaged image from the set of images.

21 Claims, 8 Drawing Sheets

US 8,737,713 B2

SYSTEM FOR FRAME SELECTION FOR OPTIMAL REGISTRATION OF A MULTI-FRAME DATASET

This is a non-provisional application of provisional application Ser. No. 61/417,944 filed Nov. 30, 2010, by J. Baumgart.

FIELD OF THE INVENTION

This invention concerns an Angiographic X-ray imaging system providing enhanced image feature visualization by selecting a set of images from a sequence of X-ray images in response to determined heart activity signal characteristics and by generating an averaged image from the set of images.

BACKGROUND OF THE INVENTION

Visualization of a stent implanted in a coronary artery is made difficult because images produced by X-ray imaging may be of insufficient quality to resolve the fine structure of an implanted stent in a single image. In order to improve image quality, known systems register a series of image frames containing landmarks that are stationary with respect to a stent and average them together. As the number of frames being registered increases, the image quality improves. An increase in the number of frames also requires an increase in the computational time and memory resources to complete a calculation, potentially beyond what is permissible within a system. Also some frames obtained in the presence of substantial cardiac motion use additional processing resources and may reduce the clarity of stent visualization. A system according to invention principles addresses these deficiencies and related problems.

SUMMARY OF THE INVENTION

A system prioritizes which frames of a multiple-frame dataset are best to use in an image registration process where there is a likelihood that some frames are less conformable to be registered images than others and/or there are limited processing resources for generation of a registered image for image enhancement of cardiac stents, for example. An Angiographic X-ray imaging system provides enhanced image feature visualization. At least one repository includes data representing a sequence of X-ray images of a portion of patient anatomy acquired over a time interval and signal data representing electrical activity of the heart of the patient over the time interval. An image data processor determines for individual images of the sequence of X-ray images, characteristics of a portion of the signal data associated with a corresponding image. The characteristics comprise at least one of, (a) a peak to peak value of a portion of the signal data associated with a corresponding image and (b) an average value of a portion of the signal data associated with the corresponding image. The image data processor selects a set of images exclusive of particular images from the sequence of X-ray images in response to the determined characteristics and generates an averaged image from the set of images.

DETAILED DESCRIPTION OF THE INVENTION

A system prioritizes images of an image sequence for use in an image registration process where there is a likelihood that some images are less conformable to be registered images than others and/or there are limited processing resources for generation of a registered image for image enhancement of cardiac stents, for example. An angiogram procedure involving imaging to provide medical images including a cardiac stent typically also involves acquiring an ECG signal. As an ECG signal samples patient cardiac activity at a substantially higher rate than an image acquisition frame rate of an angiogram, there are multiple ECG data samples acquired in the time between acquisition of images. Variations in an ECG signal are closely correlated with cardiac motion and deformation. The system identifies an advantageous image for generating a registered image as an image having a corresponding ECG signal with a low range of ECG values (i.e., maximum value close to the minimum value) indicating less cardiac deformation or movement.

Figure 1:
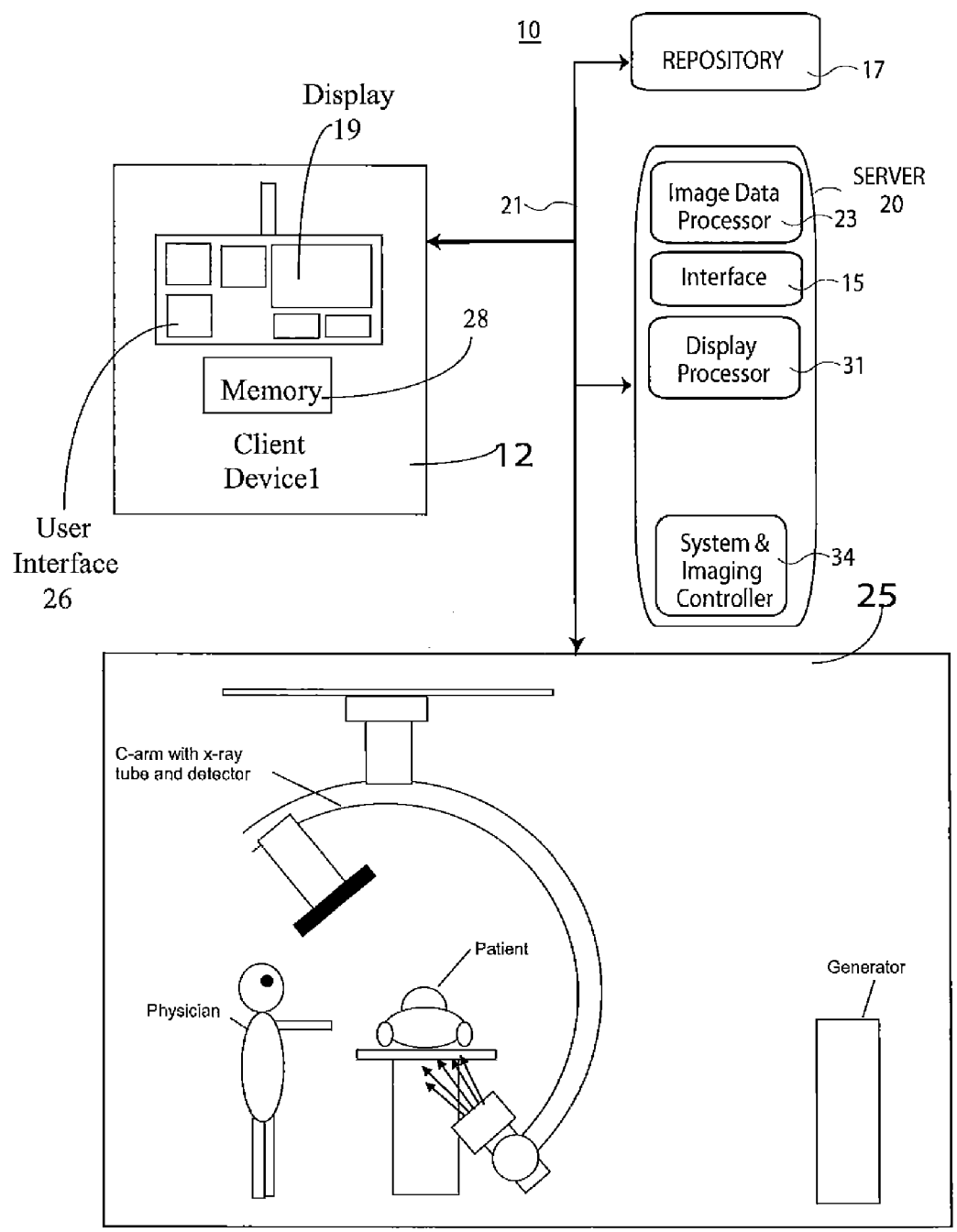
FIG. 1 shows an Angiographic X-ray imaging system providing enhanced image feature visualization, according to invention principles.

FIG. 1 shows an Angiographic X-ray imaging system 10 providing enhanced image feature visualization. System 10 includes one or more processing devices (e.g., workstations or portable devices such as notebooks, Personal Digital Assistants, phones) 12 that individually include a user interface control device 26 such as a keyboard, mouse, touchscreen, voice data entry and interpretation device, display 19 and memory 28. System 10 also includes at least one repository 17, X-ray imaging modality system 25 (which in an alternative embodiment may comprise an MR (magnetic resonance) or CT scan device, for example) and server 20 intercommunicating via network 21. X-ray modality system 25 provides patient X-ray medical images using a C-arm X-ray radiation source and detector device rotating about a patient table and an associated electrical generator for providing electrical power for the X-ray radiation system. The medical images are generated in response to predetermined user (e.g., physician) specific preferences. At least one repository 17 stores medical image studies for multiple patients in DICOM compatible (or other) data format and signal data representing electrical heart activity such as an ECG (electrocardiogram) or ICEG (intra-cardiac electrocardiogram) acquired from a patient via interface 15.

A medical image study individually includes multiple image series of a patient anatomical portion and an image series in turn includes multiple images. Server 20 includes interface 15, image data processor 23, display processor 31 and system and imaging controller 34. Display 19 presents display images comprising a Graphical User Interface (GUI). Imaging controller 34 controls operation of imaging device 25 in response to user commands entered via user interface 26. In alternative arrangements, one or more of the units in server 20 may be located in device 12 or in another device connected to network 21.

Interface 15 in conjunction with imaging system 25, acquires a sequence of X-ray images of a portion of patient anatomy over a time interval and signal data representing electrical activity of the heart of the patient over the time interval. Interface 15 stores the acquired images and heart activity signal data in at least one repository 17. Image data processor 23 determines for individual images of the sequence of X-ray images, characteristics of a portion of the signal data associated with a corresponding image. The characteristics comprise, (a) a peak to peak value of a portion of the signal data associated with a corresponding image and (b) an average value of a portion of the signal data associated with the corresponding image. Image data processor 23 selects a set of images exclusive of particular images from the sequence of X-ray images in response to the determined characteristics and generates an averaged image from the set of images.

Figure 6:
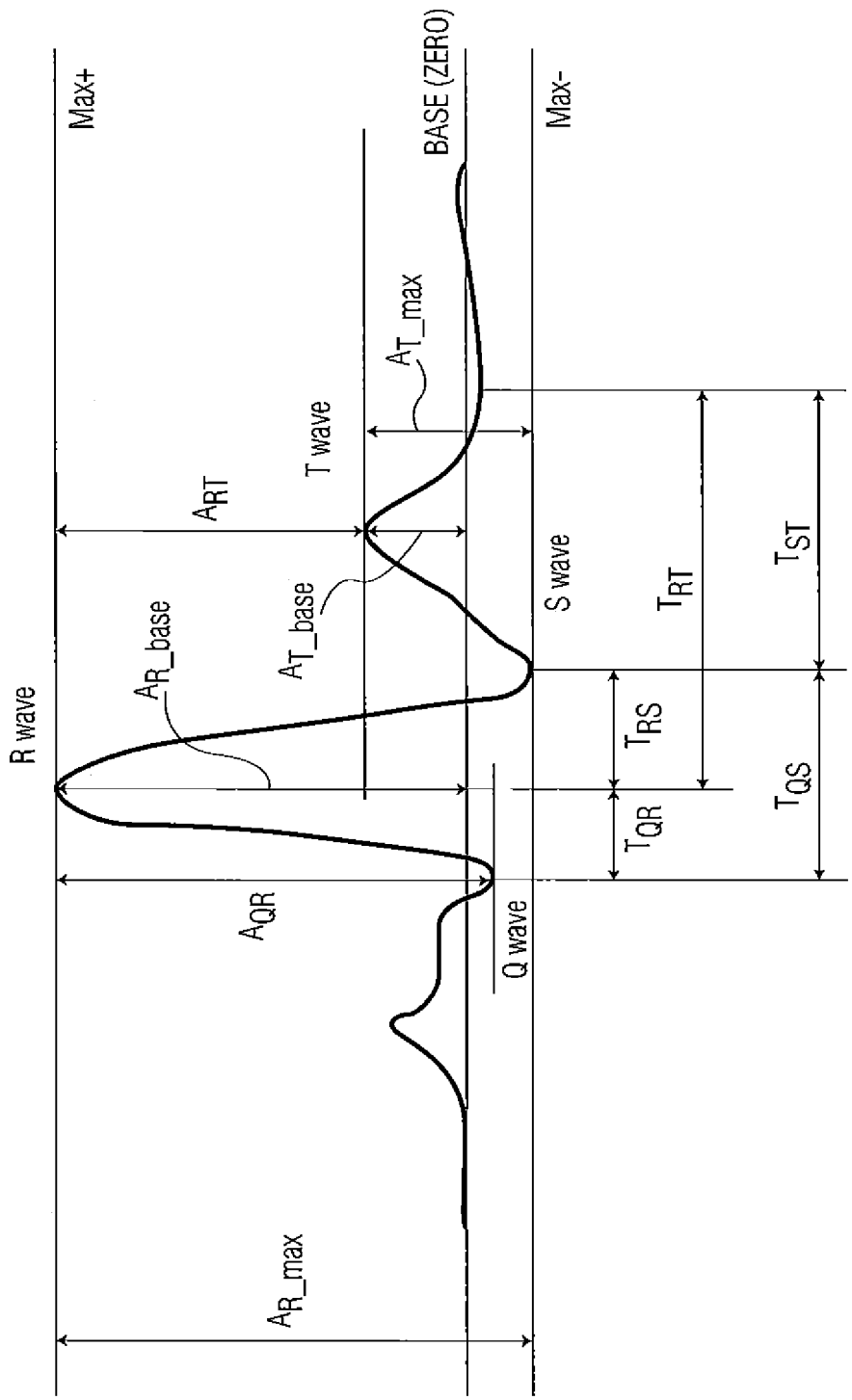
FIG. 6 shows an ECG signal representing electrical activity of the heart.
Figure 7:
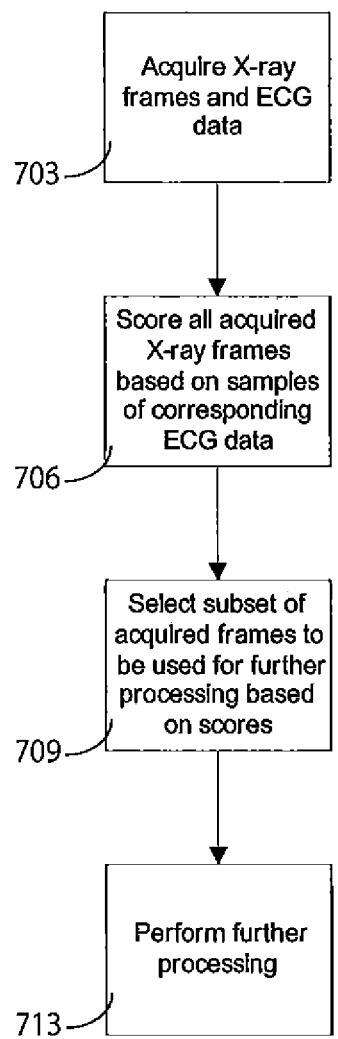
FIG. 7 shows a flowchart of a process used by an Angiographic X-ray imaging system for processing image and ECG data, according to invention principles.

FIG. 7 shows a flowchart of a process used by Angiographic X-ray imaging system 10 for processing image and ECG data. In step 703, interface 15 together with imaging system 25, acquires a sequence of X-ray images of a portion of patient anatomy over a time interval and signal (e.g., ECG signal) data representing corresponding electrical activity of the heart of the patient over the time interval. FIG. 6 shows an ECG signal representing electrical activity of the heart including a QRS complex, S wave and T wave. Image data processor 23 in step 706 derives a score value for each individual image of the acquired image sequence using sample values of the corresponding heart electrical activity (ECG) signal. The score values are used by processor 23 to identify images in the image sequence having similar score values. An advantageous image is identified as having a heart electrical activity signal with similar average value to images with which it is being registered (aligned). In one embodiment, processor 23 advantageously derives a score value of an image using the function, $$D_i = \frac{1}{1 + \sqrt{(\max(E_i) - \min(E_i))^2 + (\bar{E}_i - \tilde{E})^2}},$$ (equation 1)

where $E_i$ is an ECG data segment corresponding to image i of the sequence. $\bar{E}_i$ is the mean of the ECG data values corresponding with image i, and $\tilde{E}$ is the median value of $\bar{E}_i$ for multiple images of the sequence.

In addition, the processor 23 predicts cardiac motion by the relative position of corresponding ECG data compared with previous and subsequent R-wave peaks. In one embodiment, the processor 23 employs a target range indicating a starting and ending point of a segment of an ECG cycle. A score for likelihood of acceptable motion is derived by processor 23 from a target range of an ECG cycle, which indicates images in the middle of the target range having a higher score using, $$P_i = \frac{1}{\exp\left[\left(\frac{p_i - c}{c - p_{io}}\right)^4\right]},$$ (equation 2)

Where $p_i$ is the ECG value at the position of the ECG data corresponding to image i relative to a previous R-wave peak and a subsequent R-wave peak, $p_{io}$ is the ECG value at the low end of the target range of the ECG cycle, and c is the ECG value at the center of the target range of the ECG cycle. Processor 23 derives an overall score from the two sub scores of equations 1 and 2 by assigning a weighting preference, w, between 0 and 1 to one of the sub scores and combining the sub scores using, $$S_i = wP_i + (1-w)D_i.$$ (equation 3)

In step 709, image data processor 23, in response to the scored acquired images, selects a set of images with the highest scores for registration and averaging. The images selected are determined in response to score value and the computational resources available for processing and the maximum number of images that may be processed by the resources. In another embodiment, as an alternative to using equation 3, image selection is performed in two stages, with either equation 1 or equation 2 being used to score and reduce the number of candidate images, followed by using equation 3 to further score and reduce the remaining images. In step 713 processor 23 performs image data processing including generating an averaged image from the selected set of images.

Figure 2:
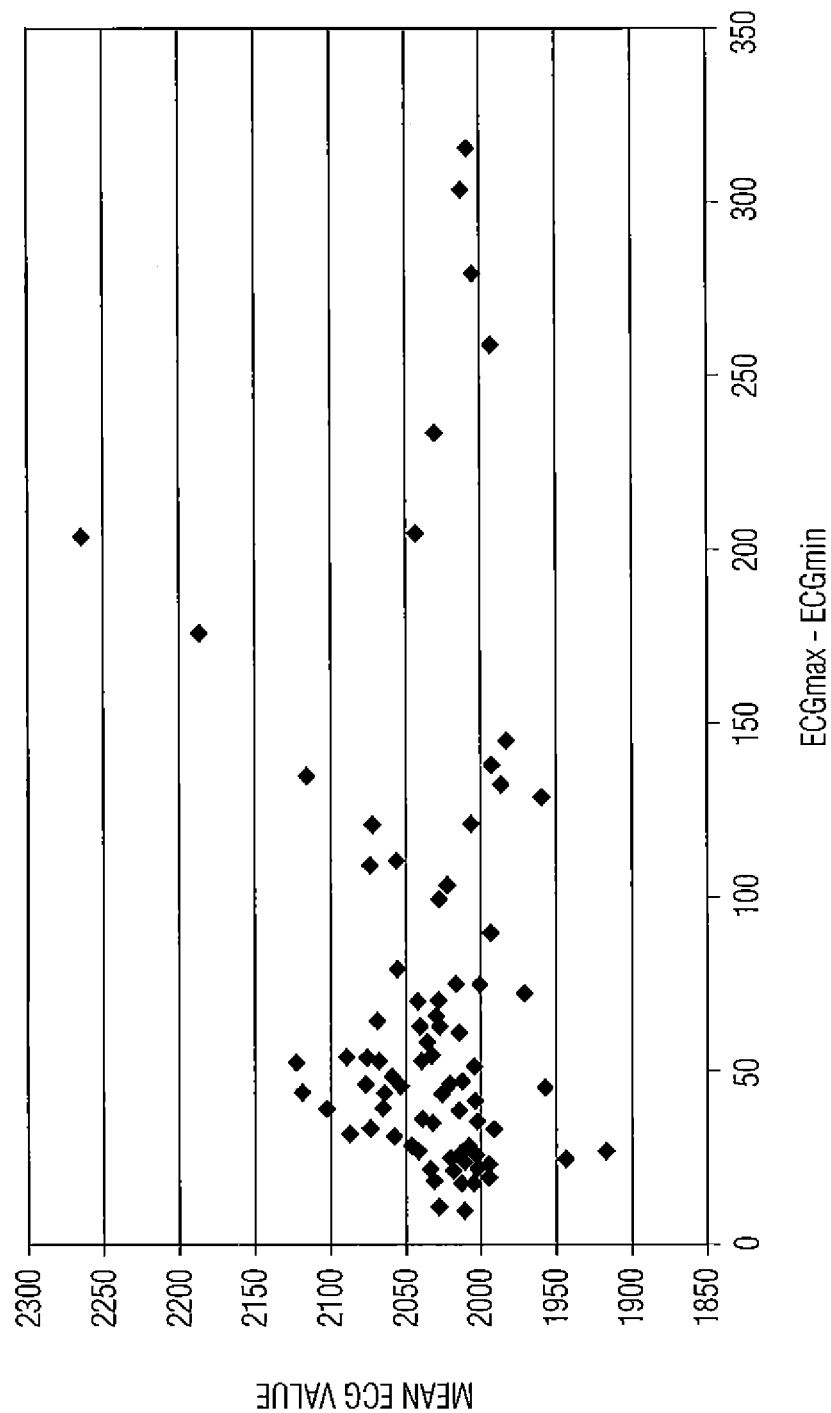
FIG. 2 shows a graph indicating maximum-minimum ECG peak to peak value (horizontal axis) plotted against mean ECG value (vertical axis) of an image sequence with each individual image of the sequence represented by a dot, according to invention principles.
Figure 3:
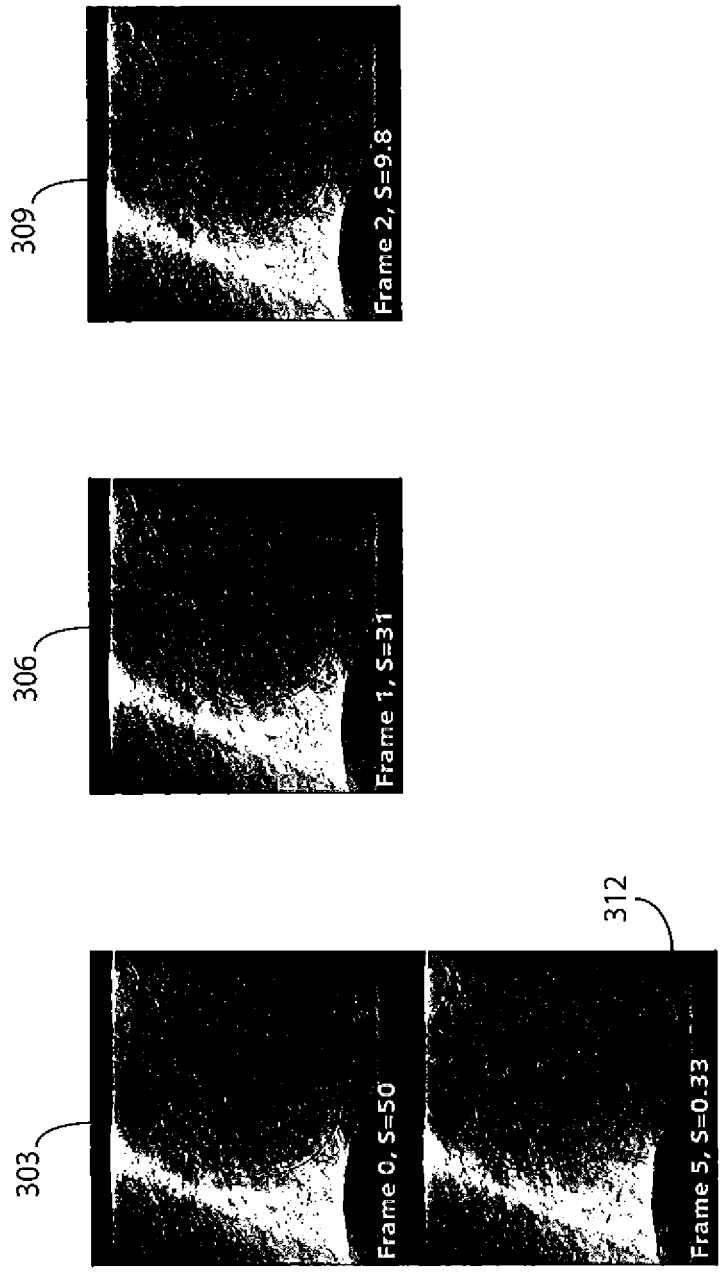
FIG. 3 shows images 0, 1, 2 of a sequence (each having a high maximum-minimum ECG peak to peak value characteristic score value) and image 5 of the sequence (having a low characteristic score value indicative of cardiac motion), according to invention principles.

FIG. 2 shows a graph of maximum-minimum ECG peak to peak value (horizontal axis) plotted against mean ECG value (vertical axis) derived for each individual image of a sequence, with each image being represented by a dot. Images in the tight cluster on the left of the graph are scored favorably using equation 1 based on ECG data content, while images represented by dots distant from the cluster are scored least favourably and are image frames that are excluded from registration by system 10. FIG. 3 shows images 0 (303), 1 (306), 2 (309) of a sequence (having a relatively high characteristic score value) and image 5 (312) of the sequence (having a relatively low characteristic score value indicative of cardiac motion or deformation). Processor 23 calculates a characteristic score using equation 1 and registers images 0 (303), 1 (306), 2 (309) and excludes image 5 (312) from registration.

Figure 4:
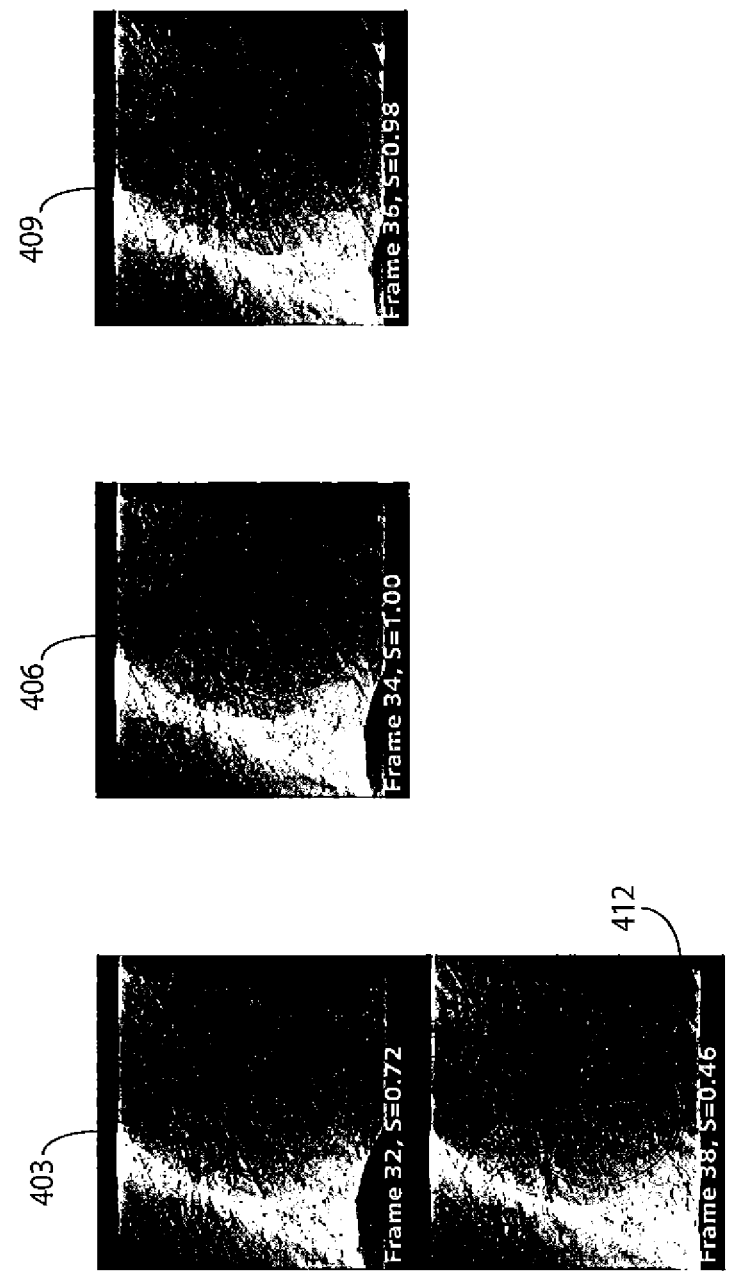
FIG. 4 shows images 32 and 38 of a sequence (having relatively high characteristic score values based on equation 2) and images 34 and 36 of the sequence (having relatively low characteristic score values indicative of cardiac motion), according to invention principles.

FIG. 4 shows images 32 (403), 34 (406), 36 (409) and 38 (412) of a sequence having characteristic scores determined by processor 23 (FIG. 1). Processor 23 (FIG. 1) derives the characteristic scores of the images using equation 2 based on position of their respective ECG data relative to preceding and subsequent R-wave peaks. In this case, the target portion of the ECG cycle is a range between 20% and 85% of heart cycle time from one R-wave peak to the next R-wave peak. The images closest to the center of this range have a relatively high characteristic score value, while images close to the edge of the range have a relatively low characteristic score value. Images 32 (403) and 38 (412) of a sequence of images are closer to the edge of the range and have relatively low characteristic score values based on equation 2 indicative of cardiac motion or deformation and images 34 (406) and 36 (409) of the sequence are close to the middle of the target ECG cycle range and have relatively high characteristic score values.

Images 32 and 38 having lower characteristic score values reflecting image feature motion when compared to frames 34 and 36.

Figure 5:
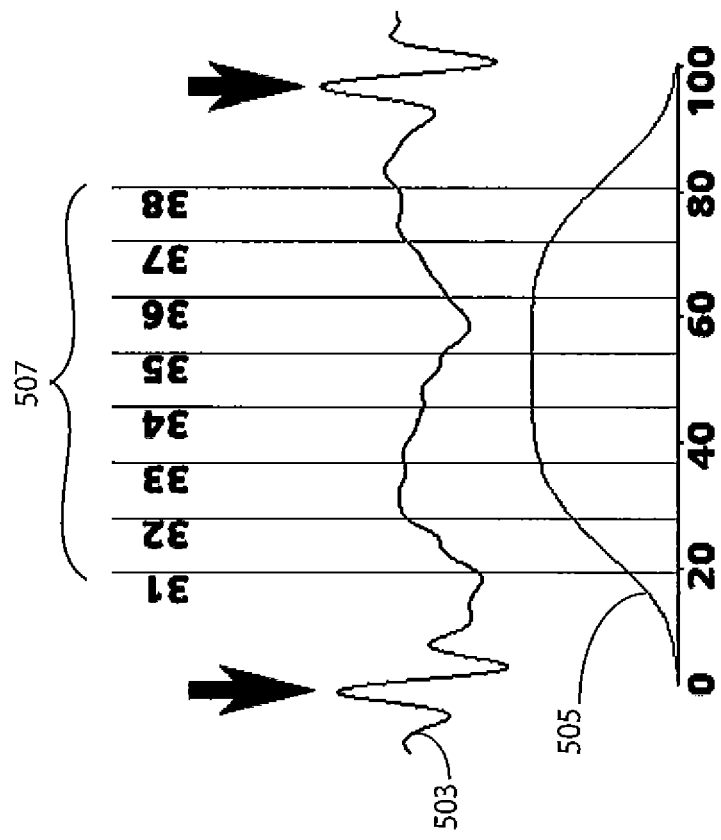
FIG. 5 shows an ECG waveform curve and a characteristic score curve derived using equation 2 marked with acquisition times of image frames 31-38, according to invention principles.
Figure 8:
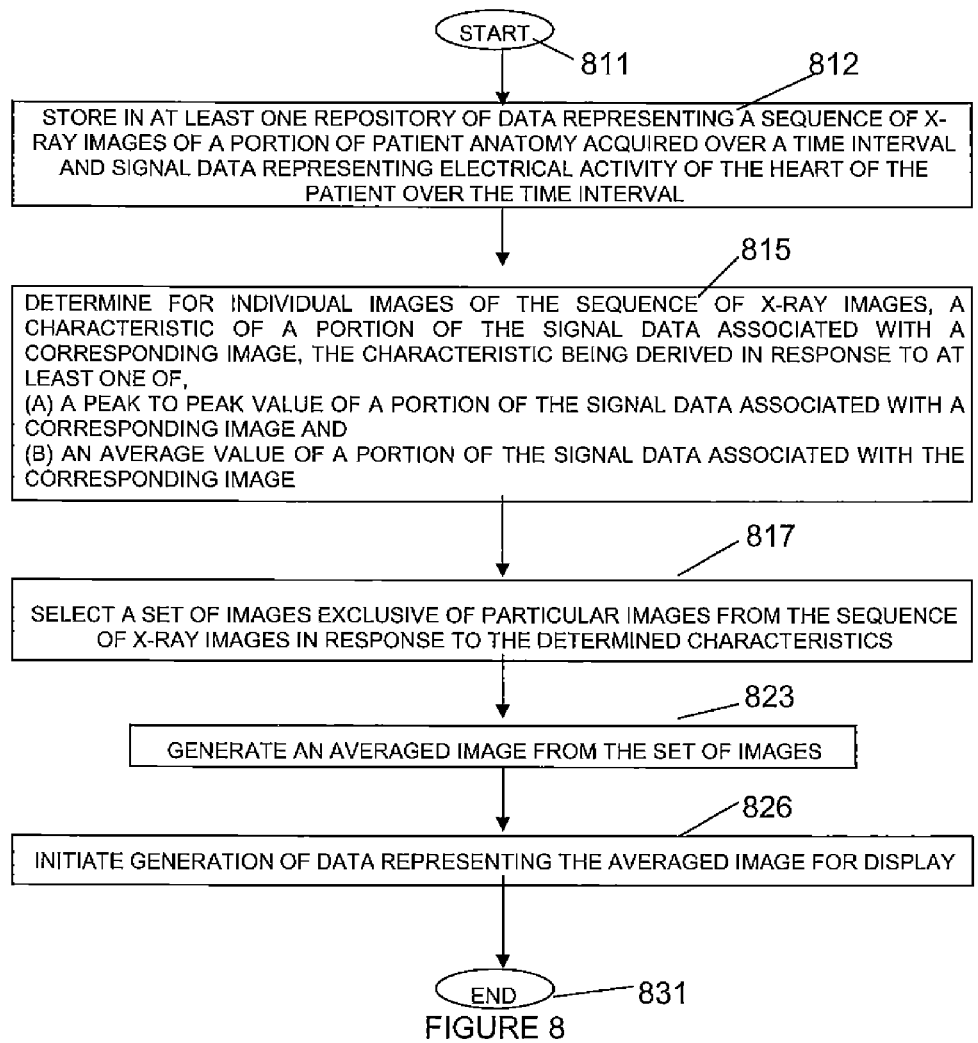
FIG. 8 shows a flowchart of a process used by an Angiographic X-ray imaging system providing enhanced image feature visualization, according to invention principles.

FIG. 5 shows an ECG waveform curve 503 showing R-wave peaks marked with arrows and a characteristic score curve 505 derived using equation 2 marked with acquisition time points of image frames 31-38 (507) of a sequence. The image frames lie between 20% and 85% points of the ECG cycle and are marked with vertical bars (image frames 31-38) and characteristic score curve 505 is derived for individual image frames using equation 2 based on the frame position in the target range of the ECG cycle. Images 32 and 38 of the sequence are closer to the edge of the range and have a relatively low characteristic score value based on equation 2 whereas images 34 and 36 of the sequence are close to the middle of the target ECG cycle range and have a relatively high characteristic score value. Images 34-36 lie in an ECG cycle range selected so the images have a relatively high characteristic score value and are used for registration whereas images outside this range are excluded from registration FIG. 8 shows a flowchart of a process used by Angiographic X-ray imaging system 10 (FIG. 1) providing enhanced image feature visualization. In step 812 following the start at step 811, interface 15 stores in at least one repository 17, data representing a sequence of X-ray images (image frames) of a portion of patient anatomy acquired over a time interval and signal data representing electrical activity of the heart of the patient over the time interval. The signal data represents electrical activity of the heart of the patient and comprises at least one of, (a) an ECG signal, (b) an Intracardiac electrocardiogram (ICEG) signal, (c) a hemodynamic signal and (d) a blood oxygen saturation SPO2 signal. In step 815, image data processor 23 determines for individual images of the sequence of X-ray images, a characteristic of a portion of the signal data associated with a corresponding image. Image data processor 23 identifies the portion of the signal data associated with a corresponding image, as a portion of the signal data acquired from the patient at a time in the time interval corresponding to a time in the interval that the corresponding image was acquired. Alternatively, processor 23 identifies the portion of the signal data associated with a corresponding image, in response to acquisition time of the portion of the signal data and acquisition time of the associated corresponding image.

The portion of the signal data comprises at least one of, (a) a heart cycle, (b) a segment of a heart cycle and a section of the signal data encompassing a time at which a corresponding image was acquired. The segment comprises at least one of, a P wave segment, a QRS complex segment, an ST segment, a T wave segment and a U wave segment. The characteristic is derived in response to at least one of, (a) a peak to peak value of a portion of the signal data associated with a corresponding image and (b) an average value of a portion of the signal data associated with the corresponding image. Processor 23 uses the determined characteristics to derive a score value for individual images of the sequence of X-ray images, the score value being indicative of whether or not an image is likely to distort an averaged image and the image data processor excludes images from the sequence of X-ray images in response to the derived score values.

Processor 23 in step 817 selects a set of images exclusive of particular images from the sequence of X-ray images in response to the determined characteristics. Image data processor 23 compares the average value of a particular image with average values of the sequence of X-ray images and excludes the particular image from the set of images in response to a determination the averaged value is insufficiently close to the average values of the sequence of X-ray images. Image data processor 23 compares the average value of a particular image with average values of the sequence of X-ray images and excludes the particular image from the set of images in response to a determination the averaged value is insufficiently close to the average values of the sequence of X-ray images.

Alternatively or additionally, processor 23 compares the peak to peak value of a portion of the signal data of a particular image with a peak to peak value of a corresponding portion of the signal data of one or more images of the sequence of X-ray images and excludes the particular image from the set of images in response to a determination the peak to peak value of the particular image is insufficiently close to the peak to peak value of the signal data of the one or more images. In step 823, processor 23 generates an averaged image enhancing visualization of an invasive instrument, for example, from the set of images. In step 826, display processor 31 initiates generation of data representing the averaged image for display. The process of FIG. 8 terminates at step 831.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouth, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system prioritizes and selects images of a multiple image sequence for use in an image registration process by identifying images for registration based on a calculated characteristic score value derived from a heart electrical activity signal and indicating less cardiac deformation or movement. Further, the processes and applications may, in alternative embodiments, be located on one or more (e.g., distributed) processing devices on a network linking the units of FIG. 1. Any of the functions and steps provided in FIGS. 1-8 may be implemented in hardware, software or a combination of both.

What is claimed is:

1. An X-ray imaging system providing enhanced image feature visualization, comprising:
   at least one repository of data representing a sequence of X-ray images of a portion of patient anatomy acquired over a time interval and signal data representing electrical activity of the heart of the patient over the time interval; and
   an image data processor for,
   determining, for each image of said sequence of X-ray images, a maximum value and a minimum value of a portion of said signal data associated with the image,
   calculating, for each image of said sequence of X-ray images, an average value based on the maximum value and the minimum value of the portion of said signal data associated with the image,
   selecting a set of images from said sequence of X-ray images by comparing said average value of a particular image with the average values of said sequence of X-ray images and excluding said particular image from said set of images in response to a determination that said average value of said particular image is insufficiently close to said average values of said sequence of X-ray images, the set of images excluding one or more images of said sequence of X-ray images, and
   generating a generated image from said set of images.

2. A system according to claim 1, wherein
   an image comprises an image frame.

3. A system according to claim 1, wherein
   said image data processor identifies said portion of said signal data associated with an image based on acquisition time of the portion of said signal data and acquisition time of the associated image.

4. A system according to claim 3, wherein
   said image data processor identifies said portion of said signal data associated with an image, as a portion of said signal data acquired from said patient at a time during said time interval corresponding to a time during said interval during which the corresponding image was acquired.

5. A system according to claim 1, wherein
   said generated image enhances visualization of an invasive instrument,
   the system further including
   a display processor for initiating generation of data representing said generated image for display.

6. A system according to claim 1, wherein
   said portion of said signal data comprises at least one of, (a) a heart cycle, (b) a segment of a heart cycle and a section of said signal data encompassing a time at which a corresponding image was acquired.

7. A system according to claim 6, wherein
   said segment comprises at least one of a P wave segment, a QRS complex segment, an ST segment, a T wave segment and a U wave segment.

8. A system according to claim 1, wherein
   said signal data representing electrical activity of the heart of the patient comprises at least one of (a) an ECG signal, (b) an Intra-cardiac electrocardiogram (ICEG) signal, (c) a hemodynamic signal and (d) a blood oxygen saturation SPO2 signal.

9. An X-ray imaging system providing enhanced image feature visualization, comprising:
   at least one repository of data representing a sequence of X-ray images of a portion of patient anatomy acquired over a time interval and signal data representing electrical activity of the heart of the patient over the time interval; and
   an image data processor for,
   determining, for each image of said sequence of X-ray images, at least one of a maximum value and a minimum value of a portion of said signal data associated with the image,
   calculating, for each image of said sequence of X-ray images, an average value based on the at least one of the maximum value and the minimum value of the portion of said signal data associated with the image,
   selecting a set of images from said sequence of X-ray images by comparing said average value of a particular image with the average values of said sequence of X-ray images and excluding said particular image from said set of images in response to a determination that said average value of said particular image is insufficiently close to said average values of said sequence of X-ray images, the set of images excluding one or more images of said sequence of X-ray images, and
   generating a generated image from said set of images.

10. A system according to claim 9, wherein
    said image data processor identifies said portion of said signal data associated with an image, based on acquisition time of the portion of said signal data and acquisition time of the associated image.

11. A system according to claim 10, wherein
    said image data processor identifies said portion of said signal data associated with an image, as a portion of said signal data acquired from said patient at a time during said time interval corresponding to a time during said interval during which the corresponding image was acquired.

12. A system according to claim 9, wherein
said generated image enhances visualization of an invasive instrument,
the system further including
a display processor for initiating generation of data representing said generated image for display.

13. A system according to claim 9, wherein
said portion of said signal data comprises at least one of, (a) a heart cycle, (b) a segment of a heart cycle and a section of said signal data encompassing a time at which a corresponding image was acquired.

14. A method for enhancing image feature visualization in X-ray imaging, comprising:
storing in at least one repository data representing a sequence of X-ray images of a portion of patient anatomy acquired over a time interval and signal data representing electrical activity of the heart of the patient over the time interval;
determining for each image of said sequence of X-ray images, a maximum value and a minimum value of a portion of said signal data associated with the image,
calculating, for each image of said sequence of X-ray images, an average value based on the maximum value and the minimum value of the portion of said signal data associated with the image,
selecting a set of images from said sequence of X-ray images by comparing said average value of a particular image with the average values of said sequence of X-ray images and excluding said particular image from said set of images in response to a determination that said average value of said particular image is insufficiently close to said average values of said sequence of X-ray images, the set of images excluding one or more images of said sequence of X-ray images; and
generating a generated image from said set of images.

15. An X-ray imaging system providing enhanced image feature visualization, comprising:
at least one repository of data representing a sequence of X-ray images of a portion of patient anatomy acquired over a time interval and signal data representing electrical activity of the heart of the patient over the time interval; and
an image data processor for,
determining, for each image of said sequence of X-ray images, a maximum value and a minimum value of a portion of said signal data associated with the image,
calculating, for each image of said sequence of X-ray images, a peak to peak value based on the maximum value and the minimum value of the portion of said signal data associated with the image,
selecting a set of images from said sequence of X-ray images by comparing said peak to peak value of a particular image with a peak to peak value of one or more images of said sequence of X-ray images and excluding said particular image from said set of images in response to a determination that said peak to peak value of said particular image is insufficiently close to said peak to peak value of said one or more images, the set of images excluding one or more images of said sequence of X-ray images, and
generating a generated image from said set of images.

16. A system according to claim 15, wherein
said image data processor identifies said portion of said signal data associated with an image based on acquisition time of the portion of said signal data and acquisition time of the associated image.

17. A system according to claim 16, wherein
said image data processor identifies said portion of said signal data associated with an image, as a portion of said signal data acquired from said patient at a time during said time interval corresponding to a time during said interval during which the corresponding image was acquired.

18. An X-ray imaging system providing enhanced image feature visualization, comprising:
at least one repository of data representing a sequence of X-ray images of a portion of patient anatomy acquired over a time interval and signal data representing electrical activity of the heart of the patient over the time interval; and
an image data processor for,
determining, for each image of said sequence of X-ray images, at least one of a maximum value and a minimum value of a portion of said signal data associated with the image,
calculating, for each image of said sequence of X-ray images, a peak to peak value based on the at least one of the maximum value and the minimum value of the portion of said signal data associated with the image,
selecting a set of images from said sequence of X-ray images by comparing said peak to peak value of a particular image with a peak to peak value of one or more images of said sequence of X-ray images and excluding said particular image from said set of images in response to a determination that said peak to peak value of said particular image is insufficiently close to said peak to peak value of said one or more images, the set of images excluding one or more images of said sequence of X-ray images, and
generating a generated image from said set of images.

19. A system according to claim 18, wherein
said image data processor identifies said portion of said signal data associated with an image, based on acquisition time of the portion of said signal data and acquisition time of the associated image.

20. A system according to claim 19, wherein
said image data processor identifies said portion of said signal data associated with an image, as a portion of said signal data acquired from said patient at a time during said time interval corresponding to a time during said interval during which the corresponding image was acquired.

21. A method for enhancing image feature visualization in X-ray imaging, comprising:
storing in at least one repository data representing a sequence of X-ray images of a portion of patient anatomy acquired over a time interval and signal data representing electrical activity of the heart of the patient over the time interval;
determining for each image of said sequence of X-ray images, a maximum value and a minimum value of a portion of said signal data associated with the image,
calculating, for each image of said sequence of X-ray images, a peak to peak value based on the maximum value and the minimum value of the portion of said signal data associated with the image,
selecting a set of images from said sequence of X-ray images by comparing said peak to peak value of a particular image with a peak to peak value of one or more images of said sequence of X-ray images and excluding said particular image from said set of images in response to a determination that said peak to peak value of said particular image is insufficiently close to said peak to peak value of said one or more images, the set of images excluding one or more images of said sequence of X-ray images; and generating a generated image from said set of images.

* * * * *